United States Patent [19]

Herber et al.

[11] Patent Number: 4,730,940
[45] Date of Patent: Mar. 15, 1988

[54] DEVICE FOR PYROMETRIC TEMPERATURE MEASUREMENT

[75] Inventors: Robert F. M. Herber; Herman J. Pieters, both of Amsterdam; Anna M. Roelofsen, Nymegen; Wouter van Deijck, Maarssen, all of Netherlands

[73] Assignee: Gruen Analysengeraete GmbH, Wetzlar, Fed. Rep. of Germany

[21] Appl. No.: 903,784

[22] Filed: Sep. 5, 1986

[51] Int. Cl.$^4$ .............................................. G01J 5/08
[52] U.S. Cl. ..................................... 374/127; 250/339; 374/128; 374/129
[58] Field of Search ..................... 374/161, 129, 128; 250/339; 374/127; 340/600

[56] References Cited

U.S. PATENT DOCUMENTS

| | | | |
|---|---|---|---|
| 4,120,200 | 10/1978 | Braun. | |
| 4,429,999 | 2/1984 | Bimberg et al. | 374/32 X |
| 4,435,092 | 3/1984 | Iucho | 374/129 |
| 4,611,930 | 9/1986 | Stein | 374/129 X |
| 4,659,234 | 4/1987 | Brouwer et al. | 374/127 X |

FOREIGN PATENT DOCUMENTS

| | | |
|---|---|---|
| 2627254 | 6/1980 | Fed. Rep. of Germany. |
| 54-63469 | 12/1980 | Japan ..................... 374/129 |

Primary Examiner—Daniel M. Yasich
Attorney, Agent, or Firm—Schwartz, Jeffery, Schwaab, Mack, Blumenthal & Evans

[57] ABSTRACT

A device for the pyrometric measurement of the temperature of a graphite tube furnace for flameless atom absorption spectroscopy is described. According to the invention, a pyroelectric detector is used as radiation receptor. The radiation flux at high temperatures is limited by a cut-off filter which starts at about $\lambda \geq 1$ μm and which, at the same time, can be constructed as radiation collector lens. It preferably consists of germanium. The detector signal is amplified in preferably three amplification stages which are connected under microprocessor control in dependence on the preselectable temperature ranges of the graphite tube furnace. A temperature measuring range from room temperature to 3,000° C. is achieved.

4 Claims, 1 Drawing Figure

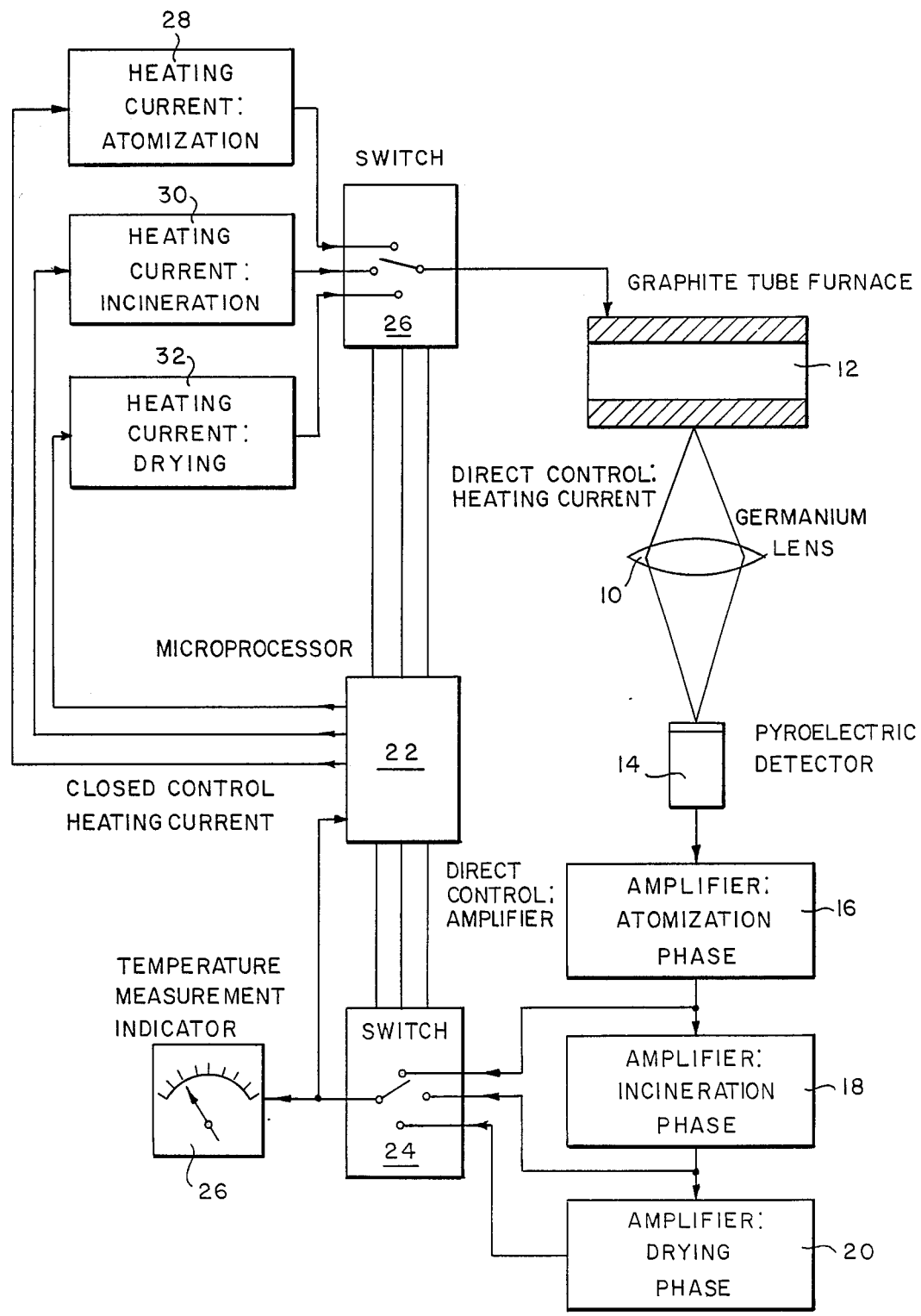

DEVICE FOR PYROMETRIC TEMPERATURE MEASUREMENT

BACKGROUND OF THE INVENTION

The invention relates to a device for the pyrometric measurement of the temperature of a graphite tube furnace for flameless atom absorption spectroscopy, having a radiation receptor for generating a temperature-dependent signal and an amplifier which follows the radiation receptor.

Devices for pyrometric temperature measurement of this type are generally known. The particular problems of applying them in flameless atom absorption spectroscopy consist in the fact that it is desirable to be able to cover with a single device the entire temperature range through which the graphite tube furnace passes through its heating up process. This temperature range extends from about 300° K. to about 3,300° K.

According to Wien's law of displacement, the maximum of the spectral intensity distribution of a black body shifts towards the short-wave spectrum with increasing temperature. In the temperature range mentioned, the maximum shifts from about 10 $\mu$m to about 1 $\mu$m. During this process, the total radiation increases proportionally to $T^4$. If the total radiation is used, a pyrometer intended for measuring this temperature range would supply an output signal which changes over several orders of magnitude within the measuring range. The dynamic ranges of the known radiation detectors and of the amplifiers following them is not nearly adequate for this purpose. For this reason, it is necessary to limit the change of the radiation flux, which is connected with the temperature change, at the radiation receptor in a suitable manner so that the output signal changes with the temperature within tolerable limits.

In Analytical Chemistry, Volume 46 (1974), pages 1028–31, a measuring arrangement is described which covers a temperature range of between 550° C. and 2,600° C. Restriction of the radiation flux is achieved by a suitable choice of the sensitivity of the radiation receptor. A photodiode is used, the sensitivity of which is between 0.62 $\mu$m and 2 $\mu$m. The spectral range below 0.62 $\mu$m is additionally cut off by a red filter. This combination represents a measuring window which is located on the short-wave slope of the spectral intensity distribution curves of the radiator and which, at the same time, determines the lower range of the temperature measurement. This is because the spectral intensity distribution curves which are valid for temperatures lower than 550° C. do not supply any further measurable contribution for wavelengths below 2 $\mu$m.

The same principle of selecting a suitable measuring window is also utilized by the measuring device described in German Patent Specification No. 2,627,254. In this arrangement, the selection was made in dependence on the lowest temperature to be measured. This was supposed to be 100° C. For this reason, the measuring window was placed on the long-wave slopes of the intensity distribution curves in the spectral range from 8 $\mu$m to 14 $\mu$m. An interference filter is provided for limiting the spectral range. All other optical and optoelectronic elements of the arrangement were selected in such a manner that they do not have any wavelength-dependence within the measuring window. A thermocouple-type detector was taken as radiation receptor and a rock salt or germanium lens was used for concentrating the radiation flux on the detector. The lenses can also be taken as carriers for applying the interference filter. The upper measurable temperature is about 2,700° C.

SUMMARY OF THE INVENTION

The invention was based on the object of extending the temperature measuring range of the devices known per se to room temperature in the lower part and to about 3,000° C. in the upper part.

According to the invention, this object is achieved by a device comprising: (a) a spectral filter having a transmissivity that begins at about $\lambda = 1$ $\mu$m and then rapidly rises and remains almost constant up to a wavelength of $\lambda \geqq 8$ $\mu$m; (b) radiation receptor means, for receiving radiation passing through said spectral filter, for generating a temperature dependent signal based on the radiation received by said radiation receptor means, wherein said radiation receptor means comprises a pyroelectric detector having a spectral sensitivity from at least about $\lambda = 1$ $\mu$m to $\lambda \geqq 8$ $\mu$m; (c) amplification means for receiving the temperature dependent signal generated by said radiation receptor means, said amplification means comprising a plurality of amplification stages, the output of each amplification stage being independently selectable; and (d) control means, coupled to said amplifier means, for selecting the output signal generated by one of said amplification stages and determining the temperature of said radiating body based on said selected signal.

DESCRIPTION OF THE PREFERRED EMBODIMENTS

In contrast to the known pyrometric measuring devices, the radiation flux emanating from the radiating body is only limited, in the subject-matter of the invention, by a cut-off filter which essentially cuts off the range of visible radiation. It is much easier to produce such a filter in comparison with the band filters hitherto used. It does not need to be produced by careful vapor-deposition techniques which, in addition, also require a selection of carrier material to match the spectral range to be filtered out.

The filtering effect required in the subjectmatter of the invention is achieved, for example, by germanium and silicon. Thin disks of these materials counteract the proportion of short-wave radiation, which rises more than proportionally at higher temperatures, in the same manner because of their transmissivity, which starts in this spectral range and drops rapidly. In addition, the thickness of the disks can be used to influence the absolute value of the radiation flux in a simple manner.

Another very significant advantage consists in the fact that from the abovementioned filter materials, lenses can be made which, because of their high refractive index, only require relatively slight curvatures, so that the lens thicknesses can also be kept down. Thus, the losses in transmissivity are also not influenced further beyond the extent desired in any case. Only a single component is therefore needed to be able to generate an image of the radiation source on the radiation receptor and at the same time to achieve the required spectral limitation of the radiation flux.

The differences in radiation intensity at room temperature and 3,000° C., which are still considerable despite the cutting off of the short-wave radiation range, require a special radiation receptor which has a correspondingly wide dynamic range in its detection sensitivity.

A pyroelectric detector has been found to be suitable for this purpose (compare Lieneweg, Handbuch der techischen Temperaturmessung [Manual of Industrial Temperature Measurement], 1976, page 358). This is a single-crystal detector having a very wide spectral bandwidth, fast response time, low noise and high load rating. A known detector material is, for example, lithium tantalate (LiTa $O_3$). In the case of encapsulated receptors, care must be taken to ensure that the window is transparent in the desired spectral range. Suitable windows are, for example, windows of magnesium fluoride (Mg $F_2$) having a transmissivity <0.2–8 μm and being made by the firm of Molectron Corp. with the type designation KRS-5 for a wavelength range of 0.6–50 μm.

Although the radiation receptor used in accordance with the invention linearly converts the high radiation intensity differences occurring into electrical signals, it is necessary to process these signals further by means of different amplification stages in the following amplifier. The amplification is selected in such a manner that, in each operating step of the graphite tube furnace (drying, incineration, atomization), in each case the highest temperature is still linearly amplified and the lowest possible temperature in each case still provides a measurable signal. An amplification factor of 190,000 times in the drying phase, of 8,000 times in the incineration phase and of 560 times in the atomization phase has been found to be particularly advantageous. These amplification stages are suitably controlled via a microprocessor which also controls the heating currents for the graphite tube furnace.

The output signals produced have approximately the same signal levels in the three operating steps due to the choice of amplification factors. This simplifies the use of the temperature measurement signals as control variables for the temperature of the graphite tube furnace.

Referring now to the drawing, an apparatus according to the present invention is shown having a germanium lens 10 which images radiation emitted from graphite tube furnace 12 onto a pyroelectric detector 14. The output of the pyroelectric detector is sent to an amplifier having three stages 16, 18, and 20. The output signal from each stage can be independently selected by a microprocessor 22 through the use of a switch 24 in order to supply the selected signal to a temperature measurement indicator 26. Microprocessor 22 also controls the amount of heating current supplied to the graphite tube furnace 12 by means of a switch 26 that selectively connects the output of three heating current sources 28, 30 and 32 to the graphite tube furnace 12. Thus, the apparatus shown in the drawing is capable of measuring the temperature of the graphite tube furnace 12 is its entire range of operation.

We claim:

1. A device for the pyrometric measurement of the temperature of a radiating body, said device comprising:
   (a) a spectral filter having a transmissivity that begins at about $\lambda = 1$ μm and then rapidly rises and remains almost constant up to a wavelength of $\lambda \geq 8$ μm;
   (b) radiation receptor means, for receiving radiation passing through said spectral filter, for generating the temperature dependent signal based on the radiation received by said radiation receptor means, wherein said radiation receptor means comprises a pyroelectric detector having a spectral sensitivity from at least about $\lambda = 1$ μm to $\lambda \geq 8$ μm;
   (c) amplification means for receiving the temperature dependent signal generated by said radiation receptor means, said amplification means comprising a plurality of amplification stages, the output of each amplification stage being independently selectable; and
   (d) control means, coupled to said amplifier means, for selecting the output signal generated by one of said amplification stages and determining the temperature of said radiating body based on said selected signal.

2. The device as claimed in claim 1, wherein said spectral filter is constructed as a collector lens which images the surface of said radiating body on said detector.

3. The device as claimed in claim 2, wherein said collector lens comprises germanium.

4. The device as claimed in claim 2, wherein said collector lens comprises silicon.

* * * * *